(12) United States Patent
Chen-Yang et al.

(10) Patent No.: US 8,735,084 B2
(45) Date of Patent: *May 27, 2014

(54) BIOCHIP ARRAY WITH A THREE-DIMENSIONAL STRUCTURE AND METHOD FOR FORMING THE SAME

(75) Inventors: Yui-Whei Chen-Yang, Tao-Yuan (TW); Jui-Chuang Wu, Tao-Yuan (TW); Yen-Kuang Li, Tao-Yuan (TW); Yun-Chu Chen, Tao-Yuan (TW)

(73) Assignee: Chung Yuan Christian University, Tao-Yuan (TW)

(*) Notice: Subject to any disclaimer, the term of this patent is extended or adjusted under 35 U.S.C. 154(b) by 1679 days.

This patent is subject to a terminal disclaimer.

(21) Appl. No.: 11/940,417

(22) Filed: Nov. 15, 2007

(65) Prior Publication Data

US 2012/0148725 A1 Jun. 14, 2012

(51) Int. Cl.
*G01N 33/53* (2006.01)
*G01N 33/547* (2006.01)
*C12M 1/34* (2006.01)
*G01N 33/552* (2006.01)
C04B 14/06 (2006.01)
C04B 14/30 (2006.01)
B01J 20/10 (2006.01)

(52) U.S. Cl.
CPC ............ *G01N 33/552* (2013.01); *C04B 14/064* (2013.01); *C04B 14/302* (2013.01); *C04B 2235/441* (2013.01); *B01J 2219/00641* (2013.01); *B01J 20/10* (2013.01)
USPC ............... 435/7.92; 435/287.2; 436/532

(58) Field of Classification Search
CPC ............... C04B 14/064; C04B 14/302; C04B 2235/441

See application file for complete search history.

(56) References Cited

U.S. PATENT DOCUMENTS

| 6,447,991 | B1* | 9/2002 | Daitch et al. ..................... 435/5 |
| 2003/0022524 | A1* | 1/2003 | Smith et al. .................. 438/778 |
| 2009/0123985 | A1* | 5/2009 | Chen Yang et al. ............ 435/176 |
| 2010/0254855 | A1* | 10/2010 | Chen-Yang et al. ......... 422/68.1 |
| 2011/0065820 | A1* | 3/2011 | Chen-Yang et al. .......... 521/102 |

OTHER PUBLICATIONS

Dai et al. Preparation of silica aerogel using ionic liquids as solvents. Chem. Commun. 2000, pp. 243-244.*
Liu et al. Preparation of porous aminopropylsilsesquioxane by a nonhydrolytic sol-gel method in ionic liquid solvent. Langmuit 2005, vol. 21, pp. 1618-1622.*
Hrubesh et al. Thin films for optical, thermal, acoustic and electronic applications. Journal of Non-Crystalline Solids 1995, vol. 188, pp. 46-53.*

* cited by examiner

*Primary Examiner* — Shafiqul Haq
(74) *Attorney, Agent, or Firm* — WPAT, PC; Justin King

(57) ABSTRACT

The present invention discloses a biochip with a three-dimensional structure. The surface of the three-dimensional mesoporous layer is chemically modified to recognize labeled DNAs, proteins, peptides, saccharides, and cells. In addition, this invention also discloses a method for preparing the biochip with a three-dimensional mesoporous layer, including a blending process, a heating process, a coating process, a gelation process, a cleaning process, a drying process, and a surface modification process.

19 Claims, 22 Drawing Sheets

BIOCHIP ARRAY WITH A THREE-DIMENSIONAL STRUCTURE AND METHOD FOR FORMING THE SAME

BACKGROUND OF THE INVENTION

1. Field of the Invention

The present invention is generally related to a biochip, and more particularly to a biochip with a three-dimensional structure and a method for forming the same.

2. Description of the Prior Art

At present, the biochip detection technology becomes increasingly important in biotechnology. The biochip detection technology can simultaneously detect various pathogens on a single chip and improve the detection limitation achieved by traditional technologies. A microarrayed biochip is generally prepared by aligning a large quantity of bio-probes (DNA's or proteins) on a chip substrate and is used for analyzing or testing samples by the hybridization of DNA-DNA or specific binding between proteins. According to the detection objectives, there are two major categories for microarrayed biochips: DNA chip and protein chip. DNA chips use nucleotide molecules as the probes to detect their complementary nucleotide fragments. DNA chips can also be categorized into complementary DNA (cDNA) chips and oligonucleotide chips, according to the length of the probes spotted on chips. cDNA chips are often used in the research of gene expressions; while oligonucleotide chips can also be used in diagnosis of pathogen and genotyping in addition to gene expression analysis.

For DNA chips, probes are immobilized on substrates and used to detect specific DNA fragments by the characteristic hybridization with complementary DNA's. DNA chips can be applied on disease detection and shorten the time for developing new medicines. DNA chip is also a powerful tool for analyzing DNA's by appropriate dye labeling in visible emission lights. By different emission wavelengths, individual target DNA can be distinguished and analyzed.

The application of biochip is vary wide, including gene expression profiling, toxicology analysis, gene sequencing, SNP identification, forensics, immunoassays, protein chip, combat biowarfare, drug screening, hard drives and microprocessors.

The improvement of detection sensitivity by modifying the substrate surfaces of traditional biochips is currently still being sought to obtain amplified signals to facilitate further analysis. Thus, a novel biochip preparation method is proposed to achieve the high-sensitivity performance.

SUMMARY OF THE INVENTION

In accordance with the present invention, a biochip with a three-dimensional mesoporous layer and a method for forming the same are provided.

The three-dimensional mesoporous material is a network polymer with nano-scaled pores, such as aerogel material. Its porosity can be as high as 95%. Due to its high porosity, it possesses a variety of characteristics: high specific surface area, low density, low heat conductivity, low sound spreading speed, low dielectric constant, and so forth. Therefore, it can be applied in various fields, such as heat insulation, catalyst, adsorbent, electrodes, electronics, detectors, etc.

The first objective of the present invention is to synthesize materials on the top of a flat substrate to form a three-dimensional mesoporous layer using the sol-gel technique.

The second objective of the present invention is to utilize the large three-dimensional inner specific surface area to recognize labeled DNAs, proteins, peptides, saccharides, and cells. Thus, the biochip with a three-dimensional mesoporous layer according to the present invention has the characteristics of high sensitivity of detection so as it would have a potential to simplify the detection equipments. For example, only data type camera (CCD) would be required instead of complicated imaging technique. Therefore, this present invention does have the economic potential for industrial applications.

Accordingly, the present invention discloses a biochip comprising a substrate and a three-dimensional mesoporous layer on top of the substrate. The surface of the three-dimensional mesoporous layer is chemically modified to recognize labeled DNAs, proteins, peptides, saccharides, and cells. In addition, this invention also discloses a method for preparing the biochip with a three-dimensional mesoporous layer, including a blending process, a heating process, a coating process, a gelation process, a cleaning process, a drying process, and a surface modification process.

DESCRIPTION OF THE PREFERRED EMBODIMENTS

Figure 1:
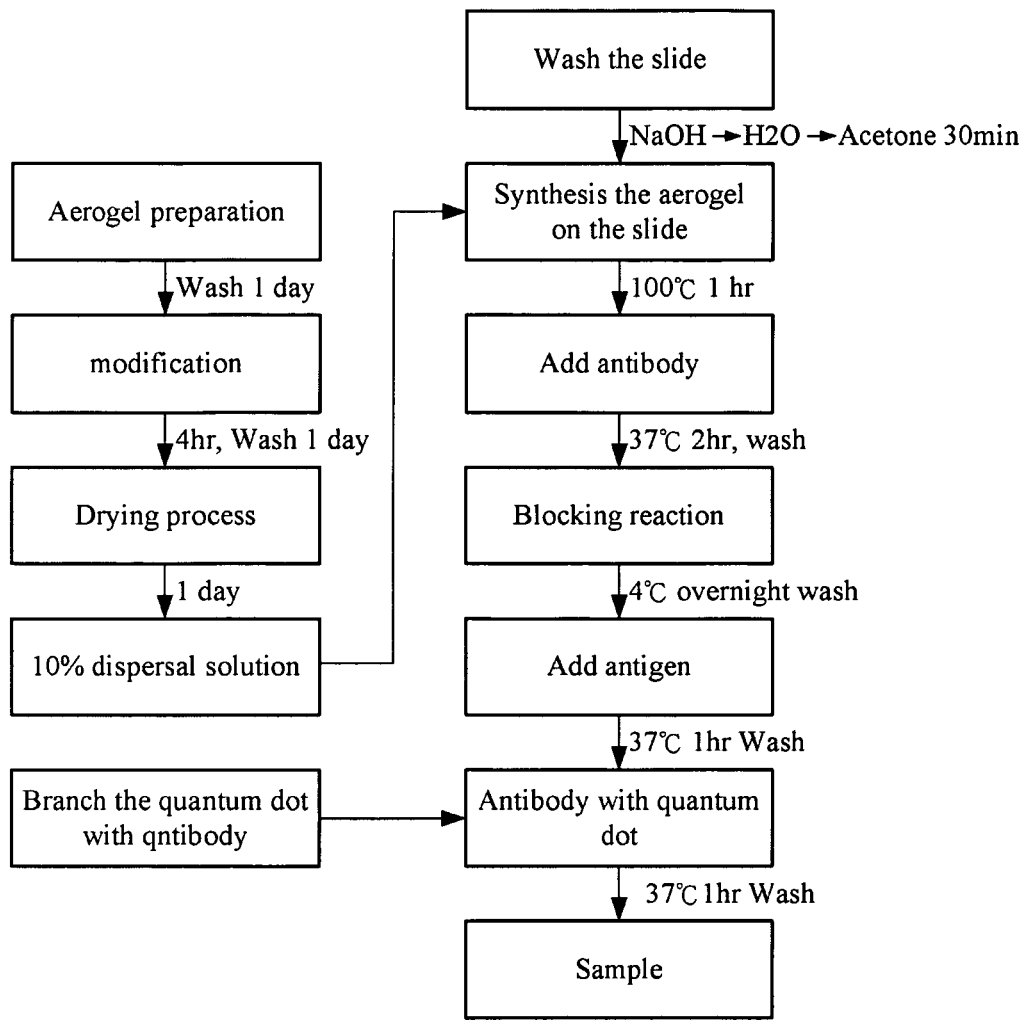
FIG. 1 is a picture showing the flowchart for forming a biochip with a three-dimensional aerogel layer according to a preferred example of the present invention.

The invention claims a biochip with a three-dimensional structure and a method for forming the same. Detail descriptions of the structure and elements will be provided as followed in order to make the invention thoroughly understood. The application of the invention is not confined to specific details familiar to those who are skilled in the art. On the other hand, the common structures and elements that are known to everyone are not described in details to avoid unnecessary limits of the invention. Some preferred embodiments of the present invention are now described in greater detail as followed. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a method for forming a biochip with a three-dimensional structure is disclosed. At first, a precursor solution is provided. The precursor solution comprises an ionic liquid, a catalyzed hydrolysis and/or condensation reagent, and at least one alkoxide monomer and/or aryloxide monomer, where the catalyzed hydrolysis and/or condensation reagent comprises one selected from the group consisting of the following or any combination of the following: alcohol, acidic compound, and alkaline compound. The ionic liquid is used as a template as well as a solvent. The central element of the alkoxide monomer and/or aryloxide monomer comprises one selected from the group consisting of the following elements: Li, Na, K, Rb, Cs, Be, Mg, Ca, Sr, Ba, Ti, Te, Cr, Cu, Er, Fe, Ta, V, Zn, Zr, Al, Si, Ge, Sn, and Pb. Next, a blending process for the precursor solution to hydrolyze and polymerize the at least one alkoxide monomer and/or aryloxide monomer until the viscosity of the precursor solution reaches a specific viscosity more than or equal to 150 cps. Then, setting the precursor solution to have the at least one alkoxide monomer and/or aryloxide monomer continue to undergo hydrolysis and condensation, so as to form aerogel.

After the aerogel is formed, the extracting process is carried out by a solvent for the aerogel to substitute the ionic liquid in pores of the aerogel. Next, a drying process is carried out to remove the solvent in pores of the aerogel. Then, a grinding process is carried out to grind the aerogel into powder, and the diameter of the aerogel powder ranges from about 10 nm to 250 nm. After the grinding process, a modification process is carried out and the internal and external surface of the aerogel powder is modified by a modifier with a specific moiety to form a modified aerogel powder. Finally, a coating process is carried out to coat the modified aerogel onto a specific region of substrate, so as to form a biochip with a three-dimensional structure. The material of the substrate comprises one selected from the group consisting of the following materials: silicon chip, glass, gold-coated glass, or polymer.

The above-mentioned coating process described as followed: firstly dispersing the modified aerogel powder in a double-distilled water to form a dispersing solution; next coating the dispersing solution on a specific region of substrate; and finally performing a baking process to remove the solvent of the dispersing solution and to enhance the adhesive force between the modified aerogel powder and the substrate, so as to form the biochip with a three-dimensional structure. In addition, the temperature of the baking process ranges from 80° C. to 120° C. .

The precursor solution also comprises an acidic compound, alkaline compound or water to catalyze the hydrolysis/polymerization of the alkoxide monomer and/or aryloxide monomer. The method for preparing the precursor solution described as followed: firstly blending the alkoxide monomer and/or aryloxide monomer and the ionic liquid together to form a first mixture; next adding an acidic compound to the first mixture to form a second mixture; and finally adding an alkaline compound to the second mixture to enhance the hydrolysis/polymerization reactions of the alkoxide monomer and/or aryloxide monomer.

The common composition of the aerogel selected from the group consisting of the following or any combination: $SiO_2$, $TiO_2$, $V_2O_5$, and $Al_2O_3$. The preferred solvent is the one with a low boiling point (less than or equal to 200° C.). The ionic liquid in aerogel pores is substituted by the solvent. Preferably, the solvent comprises one selected from the group consisting of the following: nitrile, alcohol, ketone, and water. The average pore diameter of the aerogel ranges from about 2 nm to 50 nm. The specific surface area is more than or equal to 100 $m^2/g$ and the porosity is 50%~99%.

The aerogel powder was modified by a modifier. The modifier for the modification process is an alkoxide monomer and/or aryloxide monomer with at least one specific moiety. The specific moiety comprises one selected from the group consisting of the following: amine group, hydroxyl group, carboxyl group, and epoxy group. The common modifier comprises N-[3-(trimethoxysilyl)propyl]-1,2-ethanediamine (DAMO), 3-Glycidoxypropyl-trimethoxysilane (GLYMO), 3-Aminopropyltriethoxysilane (APTS), N-(2-Aminoethyl)3-aminopropyltriethoxysilane (TMsen) and so forth. The modified aerogel powder is coated on a specific region of substrate with the coating process, so as to form a biochip with a three-dimensional structure.

According to the first example of the present invention, after the coating process, a converting process is carried out. At first, a converter that comprises a first moiety and a second moiety is provided. Then, the specific moiety of the aerogel powder is bonded with the first moiety of the converter to form a biochip having the second moiety on its surface. For example, when the modifier is N-[3-(trimethoxysilyl)propyl]-1,2-ethanediamine (DAMO), glutaraldehyde can be used as the converter to form the mesoporous layer having aldehyde group on its surface. The converter comprises one selected from the group consisting of the following: antigens, primary antibody, monoclonal antibodies, polyclonal antibodies, nucleic acids comprising monomeric and oligomeric types, proteins, enzymes, lipids, polysaccharides, sugars, peptides, polypeptides, drugs, viruses, microbes, and bioligands.

According to the second example of the present invention, after the converting process, a blocking process is carried out. At first, a blocking reagent that comprises a third moiety is provided. Then, the specific moiety of the aerogel powder is bonded with the third moiety of the blocking reagent to form a biochip having the second moiety on its surface. The third moiety of the blocking reagent reacts with specific moiety which does not react with the first moiety of converter.

According to the third example of the present invention, after the blocking process, a specific coupling process is carried out. At first, a pair of molecules that comprises a fourth moiety and a fifth moiety is provided. Then, the second moiety of the biochip is bonded with the fourth moiety of the couple to form a biochip having the fifth moiety on its surface.

The couple comprises one selected from the group consisting of the following: antigens with primary antibody, monoclonal antibodies, or polyclonal antibodies; nucleic acids comprising monomeric and oligomeric types with complementary strand; proteins, enzymes, lipids, polysaccharides, sugars, peptides, polypeptides, drugs, viruses, microbes, and bioligands with their counterpart.

According to the fourth example of the present invention, before the specific coupling process, a labeling process is carried out on one of the coupling part. At first, a labeling carrier that comprises a sixth moiety and a seventh moiety wherein conjugated with a marker. Then, the fifth moiety of the coupling labeling carrier is bonded with the sixth moiety of the labeling carrier to form a biochip having the marker on its surface. The marker comprises one selected from the group consisting of the following: fluorescence substance, phosphorescence substance, luminescence substance, enzyme, radioactive element, quantum dot, nano diamond. The labeling carrier comprises one selected from the group consisting of the following: antigens, primary antibody, labeling primary antibody, secondary antibodies, monoclonal antibodies, polyclonal antibodies, nucleic acids comprising monomeric and oligomeric types, proteins, enzymes, lipids, polysaccharides, sugars, peptides, polypeptides, drugs, viruses, microbes, and bioligands.

In the embodiment, the mentioned ionic liquids are room-temperature ionic liquids (RTIL's), and are formed by mixing an organic base with a Lewis acid. When the Lewis acid is halogenated acid, it can form a room-temperature ionic liquid but will produce halogen acid if reacting with water. Therefore, the halogenated acid is not suitable for the present invention. The Lewis acid used by the present invention is not halogenated acid so as to prepare a stable ionic liquid in water. In a preferred example, the cationic moiety in the organic base is alkyl or aryl group having the following general equation:

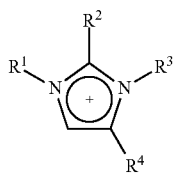

in which $R^1$, $R^2$, $R^3$, and $R^4$ are selected according to the following table.

| $R^1$ | $R^2$ | $R^3$ | $R^4$ |
|---|---|---|---|
| $CH_3$ | H | $CH_3$ | H |
| $C_2H_5$ | H | $CH_3$ | H |
| $C_2H_5$ | H | $C_2H_5$ | H |
| $CH_3CH_2CH_2CH_2$ | H | $CH_3$ | H |
| $(CH_3)_2CHCH_2$ | H | $CH_3$ | H |
| $CH_3CH_2CH_2CH_2$ | H | $C_2H_5$ | H |
| $CH_3$ | H | $CH_3OCH_2CH_2$ | H |
| $CH_3$ | H | $CF_3CH_2$ | H |
| $CH_3$ | $CH_3$ | $C_2H_5$ | H |
| $CH_3$ | $CH_3$ | $CH_3CH_2CH_2$ | H |
| $C_6H_6CH_2$ | $CH_3$ | $CH_3CH_2CH_2$ | H |
| $C_6H_6CH_2$ | $CH_3$ | $CH_3CH_2CH_2CH_2$ | H |
| $C_6H_6CH_2$ | $CH_3$ | $(CH_3CH_2)(CH_3)CH$ | H |
| $C_6H_6CH_2$ | $CH_3$ | $CH_3CH_2CH_2CH_2CH_2$ | H |
| $CH_3$ | H | $C_2H_5$ | $CH_3$ |
| $C_2H_5$ | H | $C_2H_5$ | $CH_3$ |

For example, the common organic cationic moiety comprises one selected from the group consisting of the following: 1-n-butyl-3-methylimidazolium (BMI), 1-octanyl-3-methylimidazolium (OMI), 1-dodecanyl-3-methylimidazolium (DMI), and 1-hexadecanyl-3-methylimidazolium (HDMI). In addition, the anionic moiety in the Lewis acid comprises one selected from the group consisting of the following: $BF_4^-$, $PF_6^-$, $AsF_6^-$, $SbF_6^-$, $F(HF)_n^-$, $CF_3SO_3^-$, $CF_3CF_2CF_2CF_2SO_3^-$, $(CF_3SO_2)_2N^-$ [TFSI], $(CF_3SO_2)_3C^-$, $CF_3COO^-$, and $CF_3CF_2CF_2COO^-$. When the cationic moiety to be used is determined, the anionic moiety in the Lewis acid can be adjusted to control hydrophilicity/hydrophobicity. For example, BMI-BF4 is hydrophilic and BMI-TFSI is hydrophobic.

For instance, alkyloxide monomer is used as an example. Alkyloxide monomer is hydrolyzed to form hydrophilic silanol (—Si—O—H). Thus, the hydrophilic ionic liquid and silanol are tended to attract to each other and can stabilize the formation of silicon oxide structure so as to obtain more stable three-dimensional silicon oxide mesoporous material. In this embodiment, the weight of the ionic liquid is about 10%~70% weight of the at least alkoxide monomer and preferably about 20%~50%. When the added amount is more than the upper limit, the sol concentration is reduced and the gelation is slow to result in unstable structure.

In this embodiment, the immunoassay carrying out on the biochip with a three-dimensional structure comprises one selected from the type consisting of the following: direct immunoassay, indirect immunoassay, sandwich immunoassay, competitive immunoassay, immuno Polymerase Chain Reaction, and immuno Rolling Cycle Amplification.

EXAMPLE

According to a preferred example of the present invention, the method for forming a biochip with a three-dimensional aerogel layer is provided. The method comprises the following steps.

(1) Wash the Slide:

Immerse the slide in the NaOH solution and shake by Sonicator for 30 min. Then replace NaOH solution with distilled water and vibrate for 30 min again. Lastly, replace distilled water with Acetone and again vibrate for 30 min. Take the slide out and dry them by oven.

(2) Aerogel Preparation:

Mix $BMIC-BF_4$ with water and methanol first, then mix with TEOS again quickly. After it gets well aging, wash the resulting sample and dry it in a freeze drying process. Lastly, grind the sample to powder for further usage.

The Aerogel chemical reaction equation is shown as below:

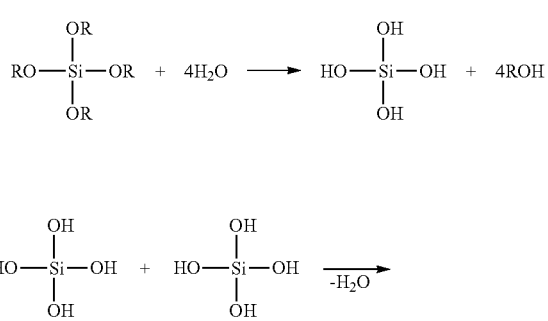

-continued

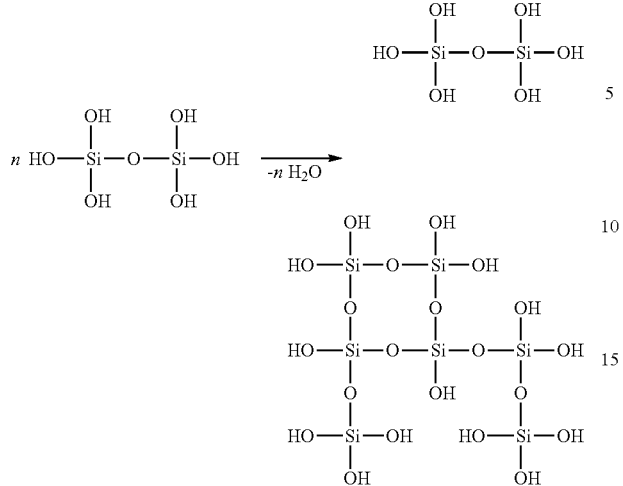

(3) Modification of the Amino Base in Aerogel:

Mix the Aerogel powder with 2% DAMO solution well and keep stirring for 1 hour. Filter the mixture and wash it with ethanol for 24 hours. Afterward, it is dried by a freeze drying process.

(4) Dropping the Aerogel on Slide

Prepare the 10% dispersal solution by dispersing the modified Aerogel in double-distilled water and keep stirring the mixture with a magnetic bar. Drop 2 μl of the dispersal solution onto the slide by a pipette.

(5) Modification of the Quantum Dot:

Prepare the SBB buffer solution: 3.09 g boric acid+19.07 g sodium borate. Adjust the pH to 9 with NaOH or HCl solution.

Calculate the amount of EDC, PEG and sulfo-NHS required. Put the required amount of the compounds in a microtube and record the amount in the microtube. Afterward, according to the amount in the microtube, calculate the volume of buffer needed. The next steps will be to mix the required ratio of quantum dot with the buffer. First of all, put PEG in the buffer and vibrate until it dissolves completely. The next step is to mix EDC with the buffer very quickly and add the quantum dot to react immediately. Then mix sulfo-NHS with the buffer. Lastly, add the quantum dot into the sulfo-solution and add the PEG solution immediately.

Vibrate and shake the whole mixture in a 4° C. refrigerator for 2 hours. After the reaction is complete, filter the solution by a molecular sieve. The residue solution is the quantum dot with a branch. The reaction of quantum dot is shown below:

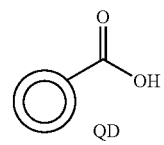

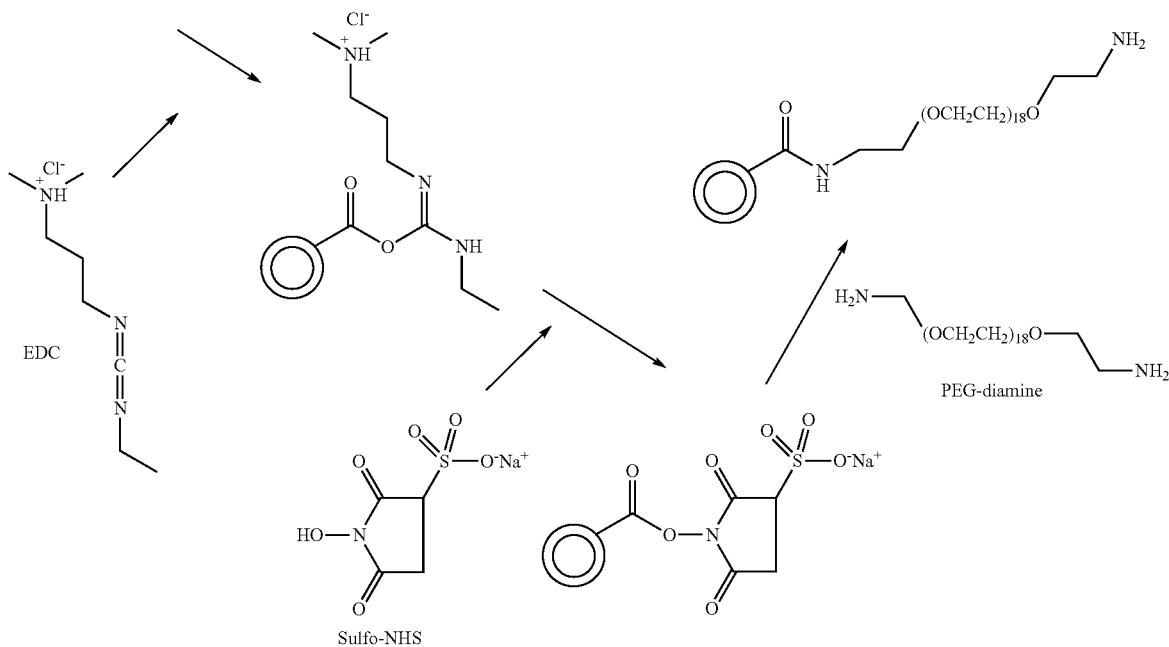

(6) Conjugate antibody with quantum dot:

PBS buffer is prepared by dissolving 0.24 g $KH_2PO_4$, 1.44 g $Na_2HPO4$, 0.2 g KCl and 8 g NaCl with double-distilled water. Then adjust the pH to 7.5 with NaOH or HCl solution. The washing buffer is prepared by adding 20.5 μl Tween 20 into 580 ml PBS buffer and mixing well.

Mix the required amount of antibody with the quantum dot. Slightly vibrate the solution and then mix in a 4° C. refrigerator for overnight. The conjugation reaction of quantum dot and antibody is shown as below:

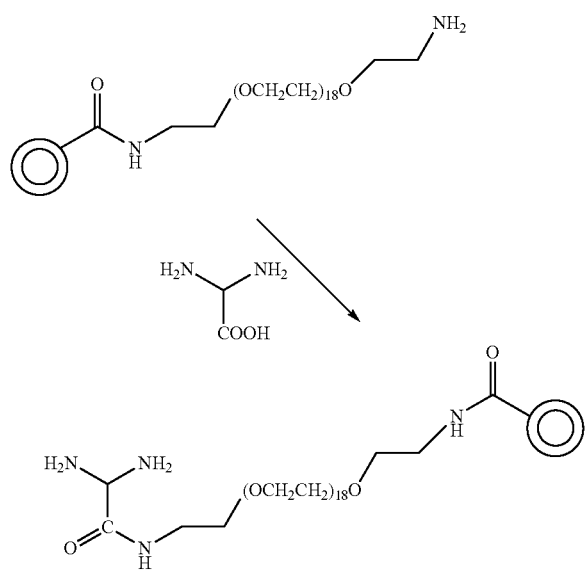

(7) Immobilization of Antibody and loading Antigen on Biochip

Drop 1 μl of capturing antibody (Mouse anti-Human IL-6) in various concentrations on a specific area of the slide. Leave the slide in a 37° C. oven for 2 hours. Immerse the slide into wash buffer and shake for 1 minute. Purge and refill the wash buffer and repeat the wash for 3 times.

For the blocking step: spread 1% BSA in PBS on the slide. Place the slide in a humid box and leave the box in a 4° C. refrigerator for overnight. Afterward, immerse the slide into wash buffer and shake for 1 minute. Purge and refill the wash buffer and repeat the wash for 3 times.

Drop 1 μl of the antigen (Human IL-6) on the same aerogel dots on the slide. Leave the slide in a 30° C. oven for 1-hour incubation. Then immerse the slide into wash buffer and shake for 1 minute. Purge and refill the wash buffer and repeat the wash for 3 times.

Drop 1 μl of the report antibody (Rabbit anti human, IL-6) conjugated with quantum dot on the same aerogel dots on the slide. Leave the slide in a 30° C. oven for 1 hour incubation. Then immerse the slide into wash buffer and shake for 1 minute. Purge and refill the wash buffer and repeat the wash for 3 times. Lastly, drop 1 μl of the pure quantum dot on the positive-control spot on the slide.

After steps (1) to (7) are completed, the slide with Aerogel is formed with a white appearance on the top. This area is the sample evaluation region.

Figure 2:
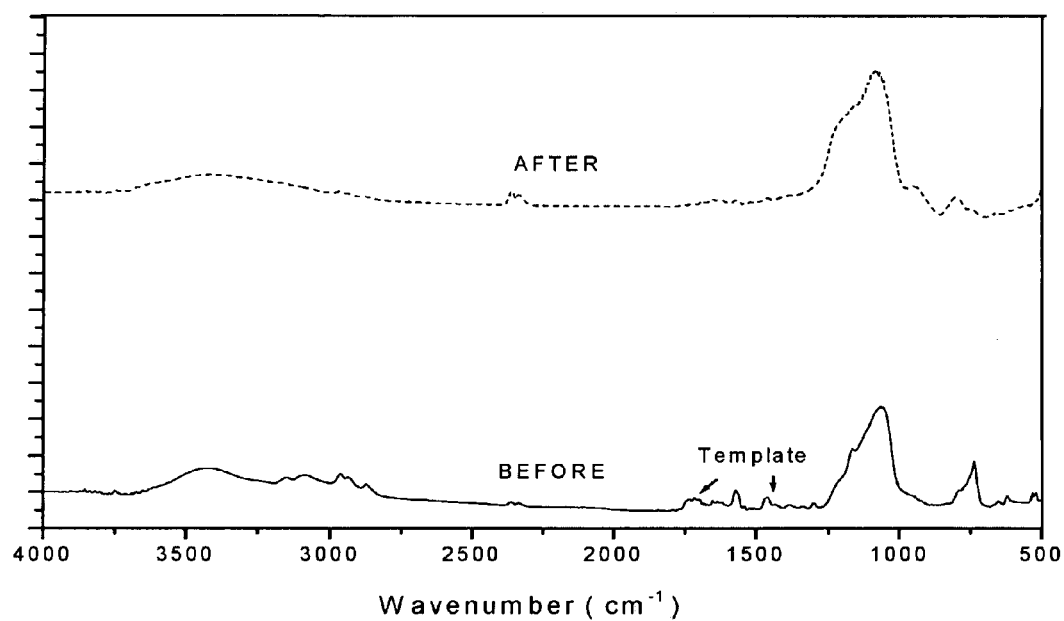
FIG. 2 is the absorption spectrum of FTIR after and before remove the solvent in three-dimensional aerogel layer according to a preferred example of the present invention.

FIG. 2 is the analytic result of the infrared absorption spectrum of Aerogel structure. This result indicates that there is two —OH bonding absorption peaks between 3200~3700 $cm^-$ and 1620~1640 $cm^{-1}$. The absorption peak between 3200~3700 $cm^{-1}$ is because of the O—H bonding vibration. The absorption peak of the 930~950 $cm^{-1}$ is because of the ≡Si—OH bonding vibration. The other peaks between 1000~1200 $cm^{-1}$, 780~820 $cm^{-1}$ and 430~460 $cm^{-1}$ are caused by the bonding vibration of ≡Si—O—Si≡.

Figure 3:
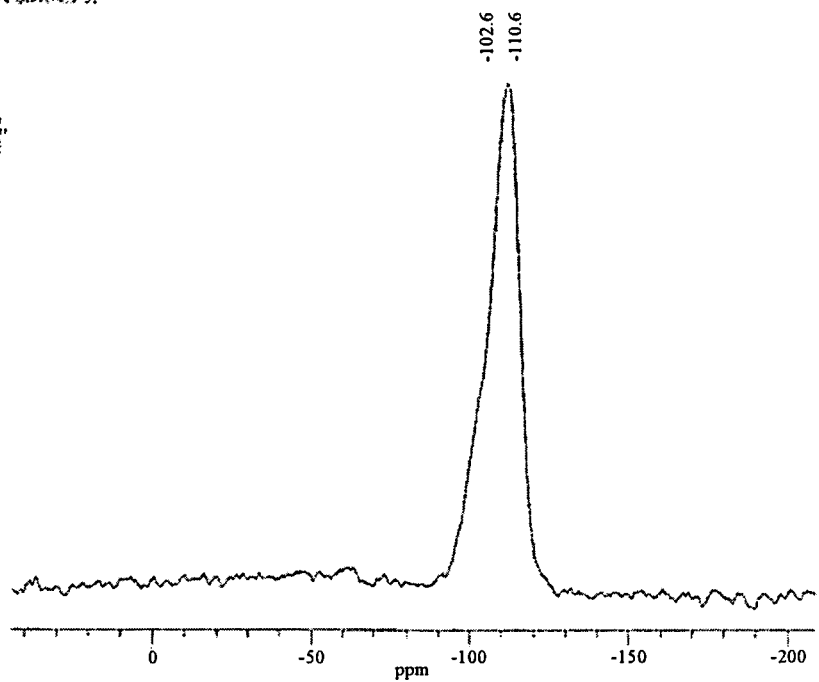
FIG. 3 shows the analysis result of the unmodified three-dimensional aerogel layer according to a preferred example of the present invention by the $^{29}Si$ solid-state nuclear magnetic resonance spectrometer.

The $^{29}Si$ solid NMR was utilized to analyze Si environment in Aerogel and clarify the bonding condition of the network structure synthesized from TEOS by sol-gel polymerization. According to the analysis result of Silica Aerogel by the $^{29}Si$ solid NMR spectrum, the characteristic absorption peak appears between −99~−102 ppm when the silicon was with 3 Si—O—Si linkages (Q3). As well, the characteristic absorption peak between −102~−110 ppm will appear when the silicon was with 4 Si—O—Si linkages (Q4). The analysis result of $^{29}Si$ solid NMR spectrum (FIG. 3) showed that most of the Si atoms in Aerogel were Q4 type and peaked at −111 ppm. Small fraction of the Si atoms in Aerogel was Q4 type and peaked at −102 ppm. This result indicated that Silica Aerogel was in formation of a stable silica network structure.

Figure 4:
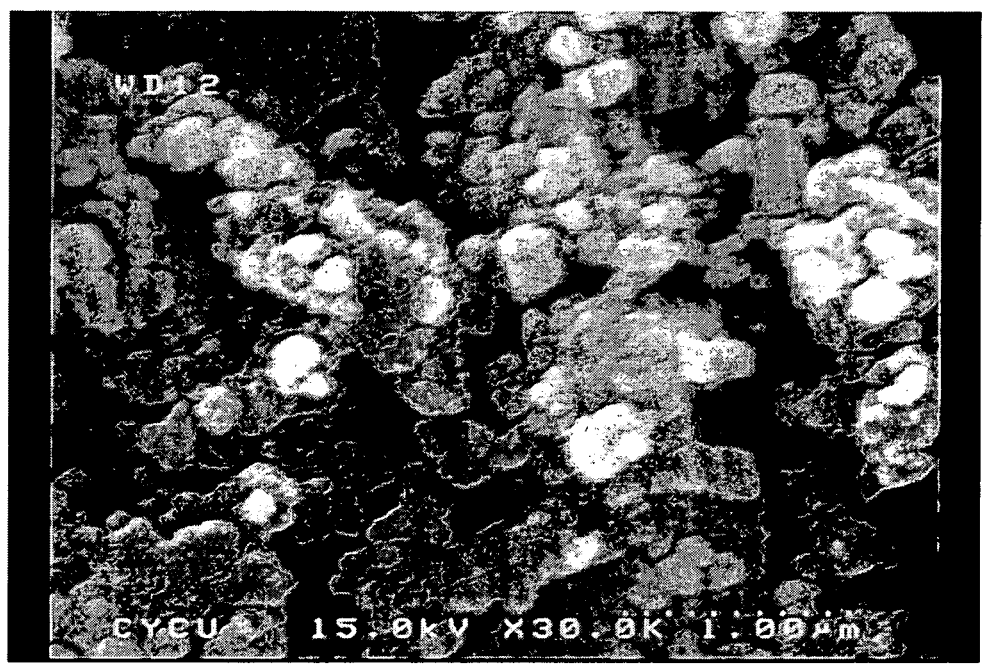
FIG. 4 shows a SEM (scanning electron microscope) images of the surface of the three-dimensional aerogel layer (amplification factor=3000) according to a preferred example of the present invention.
Figure 5:
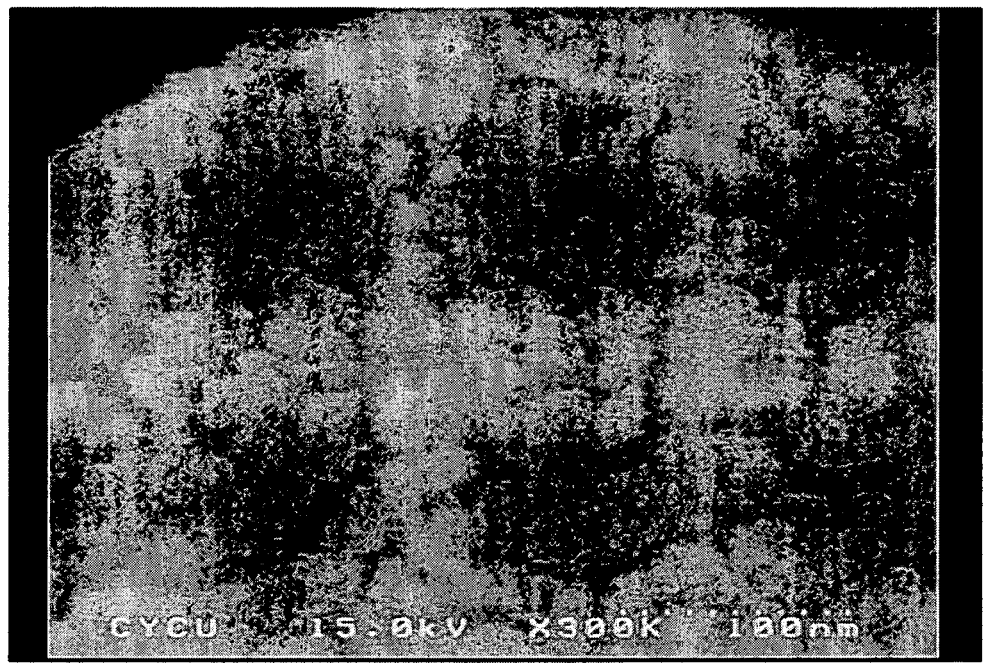
FIG. 5 shows a SEM (scanning electron microscope) images of the surface of the three-dimensional aerogel layer (amplification factor=3 0 0 0 0 0 ) according to a preferred example of the present invention.

As shown in FIGS. 4 and 5, the SEM image of Silica Aerogel cross section (FIG. 4, 30 k fold of magnification) indicated that the microstructure of the aerogel was with a spherical aggregates conformation. Furthermore, the spherical shape aggregate was composed by many tiny silica particles (FIG. 5, 300 k fold of magnification). The size of silica particles was around 20-30 nm, which verified that the Aerogel was a nano-sized material.

Figure 6:
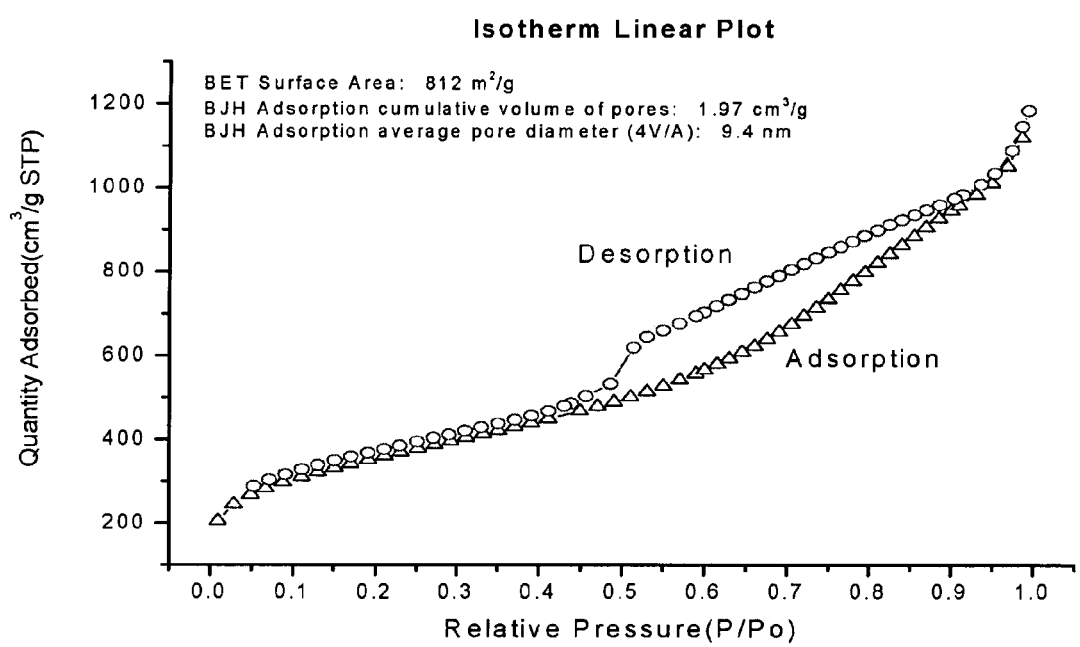
FIG. 6 is a $N_2$ Adsorption/Desorption Analyzer curve of the three-dimensional aerogel layer modified by 10% GLYMO according to a preferred example of the present invention.
Figure 7:
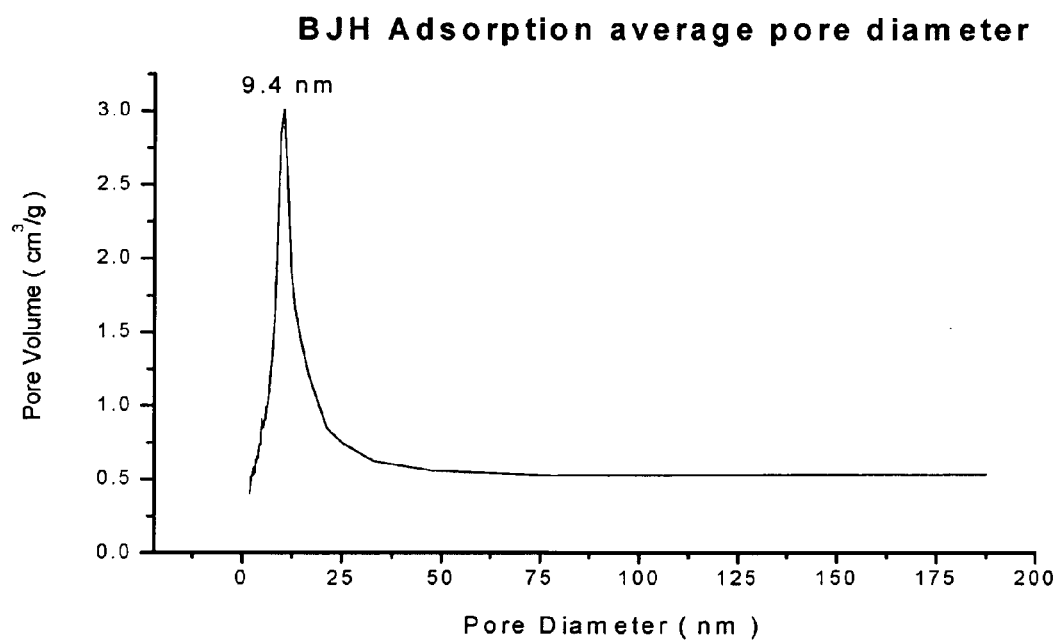
FIG. 7 is the sharp curve presenting the pore distribution of the three-dimensional aerogel layer according to a preferred example of the present invention.

Adsorption/Desorption Isotherm analysis measured the properties of porous materials. The Adsorption/Desorption Analyzer utilized inert gas (nitrogen) to measure the pore size, surface area, pore volume and pore structure of porous materials. The adsorption extent was related to the property of the sample and absorbed gas, and is a function of pressure (or concentration) and temperature. The gas adsorption quantity (per gram of sample) is usually plotted against $P/P_0$ under a constant temperature, where $P_0$ is the saturated vapor pressure of the analysis gas at the experimental temperature. The plotted curve is generally named Adsorption/Desorption Isotherms. Base on FIG. 6, the $N_2$ Adsorption/Desorption isotherm curve for Silica Aerogel, Silica Aerogel was with 812 $m^2/g$ surface area, 1.97 $cm^3/g$ pore volume, and 9.4 nm average pore size. Besides, the sharp curve in FIG. 7 indicated that the distribution range of pore sizes on Silica Aerogel is very narrow.

Figure 8:
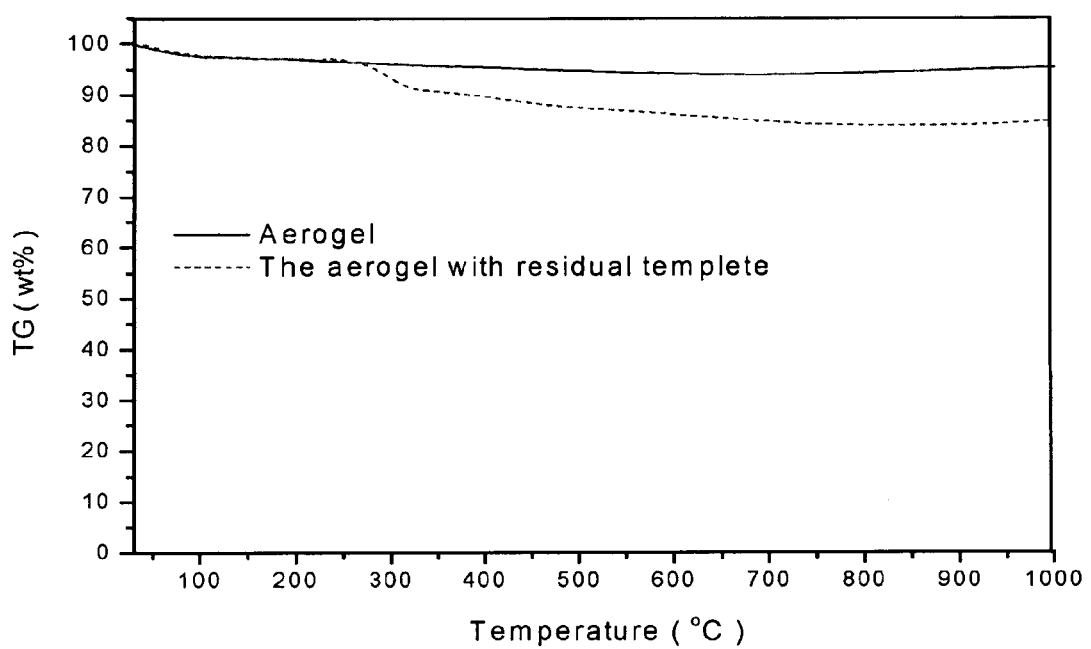
FIG. 8 shows the TGA comparison data of the three-dimensional aerogel layer before/after modification according to a preferred example of the present invention.

FIG. 8 showed the TGA curve of Silica Aerogel (detection condition: N2 at T=30~1000° C., temperature increasing rate=10° C./min). The solid line showed that 2.6% weight of Silica Aergel was lost when the temperature was lower than 100° C. The lost weight might be from the moisture on the surface. The weight loss increased to 6.2 wt % when the temperature reached 1000° C. The lost weight might be from hydroxy-silica bases which was not completely hydrolyzed or condensed on the surface of the Silica Aerogel. The dotted line showed the unremoved template residuum, which started to crack out the aerogel when the temperature reached to 265° C. This was also a way to verify if the washing step is complete.

Figure 9:
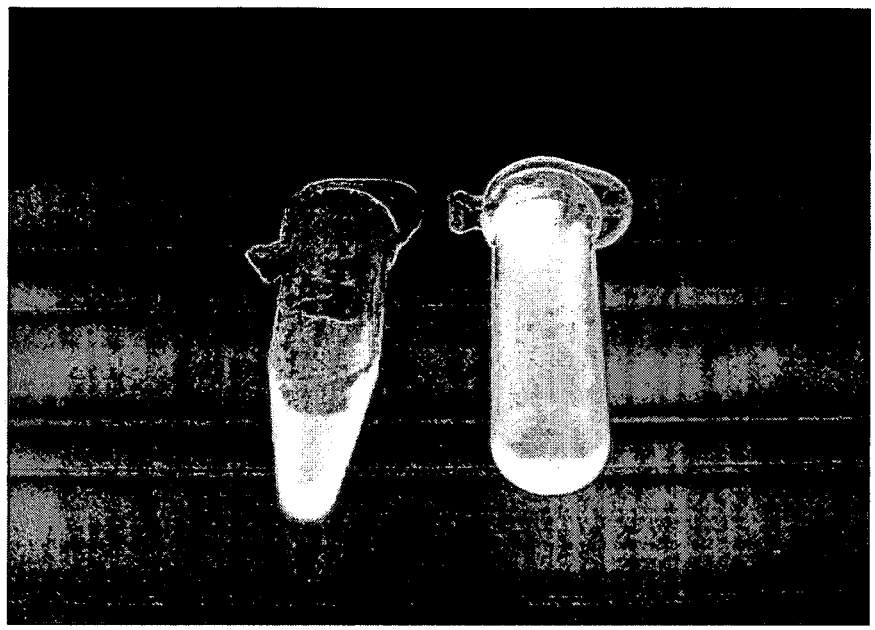
FIG. 9 shows the picture taken by a digital camera of the quantum dot under UV light excitation according to a preferred example of the present invention.

Different sizes of nano-quantum dots will show different fluorescence under UV light. FIG. 9 showed the picture taken by a digital camera of the quantum dot under UV-light excitation. The excitation wavelength was around the green light region.

Figure 10:
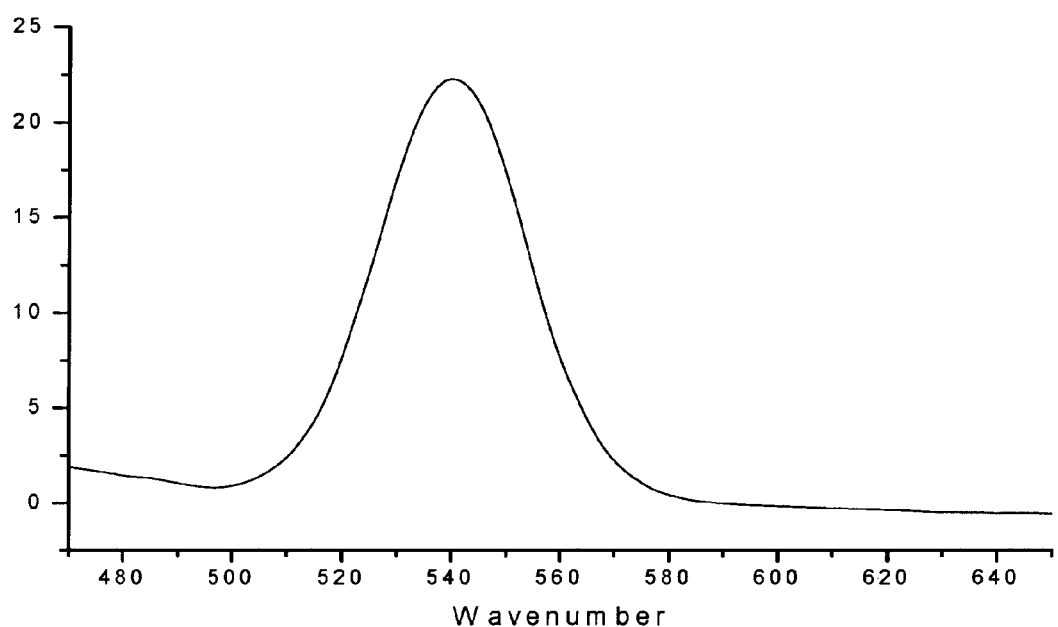
FIG. 10 shows the result of the modified quantum dot of the Fluoresce Spectrometer according to a preferred example of the present invention.

The surface modification of the quantum dot added an amino group on the hydrophilic surface of the quantum dot. The amino group was further conjugated with the carboxyl group on an antibody to become an indication marker in the experiment. FIG. 10 showed the result of the modified quantum dot by the Fluorescence Spectrometer. The excitation wavelength switched to 540 nm, because of the addition of amino group on quantum dot's surface. This result indicated that the modification was successful.

Figure 11:
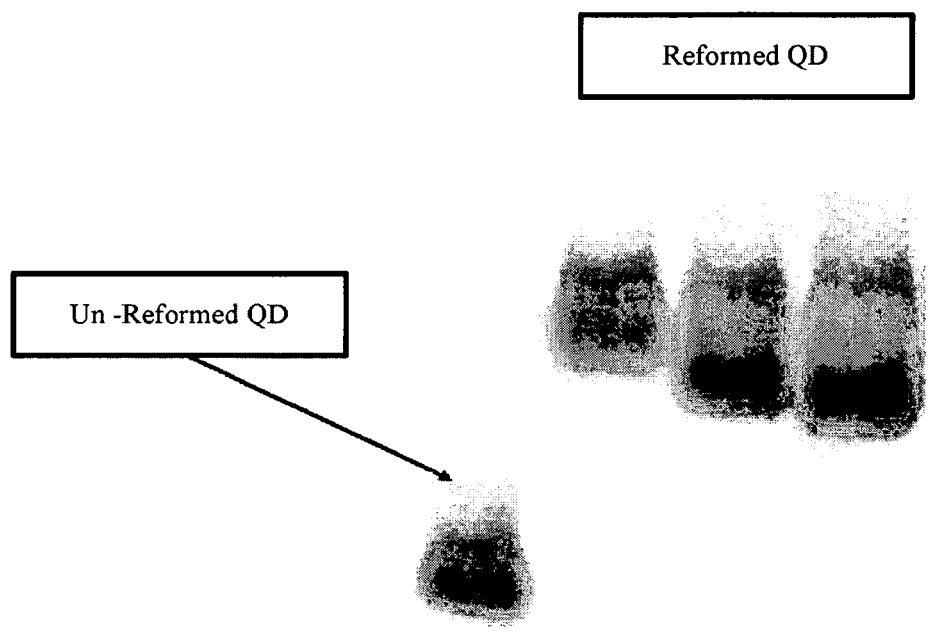
FIG. 11 shows the gel electrophoresis of the quantum dot before and after modification according to a preferred example of the present invention.

Heavier molecules will migrate slower than the light ones during the electrophoresis process at the same voltage and time. The modified quantum dot was heavier in molecular weight than the unmodified one, so the electrophoresis can be a methodology to detect if the surface modification was is successful. From FIG. 11, the slower migration of the modified quantum dot than the unmodified one suggested that the surface modification was successful.

Since adding the buffer solution during the modification process changed the original concentration, measurement of the resulting concentration became necessary after the modification process. The light absorption was measured at 527 nm on modified quantum dots. The concentration was further calculated by the absorption values by the formula:

$$C=A/\in L$$

A is the Absorption value; $\in$ is the absorption constant $(M\text{-}nm)^{-1}$; L is the particle diameter (nm). Using the right tube in FIG. 9 as the example, the measured data were
A=0.04
L=0.512
$\in$=77794
Substitute the formula with the above data, $$0.04/(777941 \times 0.512) = 1.00 \times 10^{-6}$$

The concentration will be calculated as $1.00 \times 10^{-6}$ M

The protein biochips demonstrated in this invention was characterized by the specificity of the three-dimensional structure between protein-protein or protein-small molecules.

Figure 12:
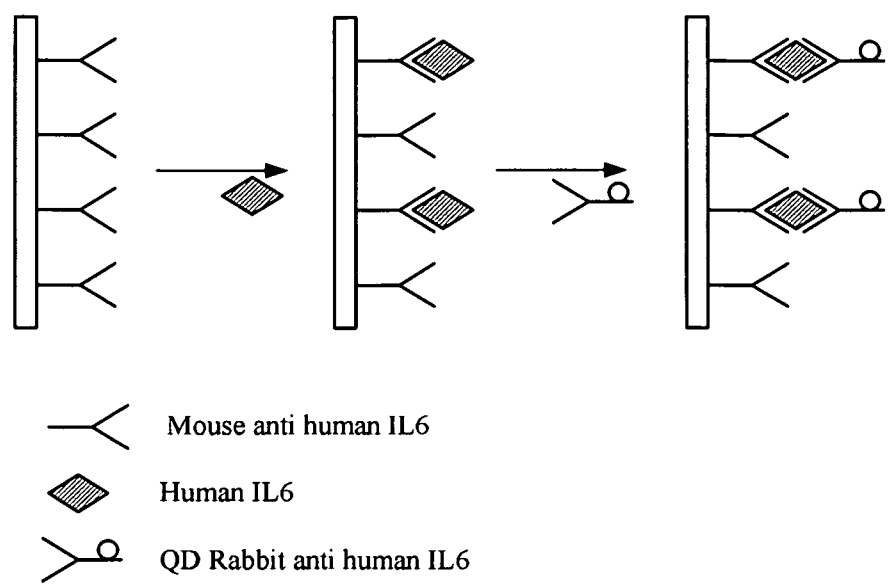
FIG. 12 shows the flowchart of Sandwich Immunoassay according to a preferred example of the present invention.

As shown in FIG. 12, this experiment applied the Sandwich Immunoassay by immobilizing the capturing antibody on the aerogel's surface to be capable of capturing its affinity antigen. After that, the report antibody was added to report the detection by its labeled quantum dot. In the case that the target antigen was not present, the sandwich immunoassay will not be carried out such that the report antibody will be unable to stay to report the detection. The fluorescence scanner will not read out fluorescent signals.

The fluorescence chip scanner, model GenePix 40000B, utilized a dual laser-scanning system to generate the real-time images. The images were composed with standard 24-bite colors. The default wavelengths setting of scanner system were at 635 and 532 nm.

Figure 13:
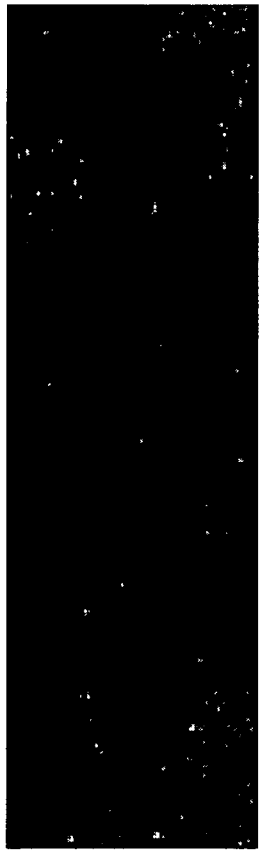
FIG. 13 shows the images of the washed blank slide according to a preferred example of the present invention.
Figure 14:
FIG. 14 shows the image of a two-dimension chip after the amino functional-group modification process according to a preferred example of the present invention.

FIG. 13 showed the washed blank slide. The background value was extremely low in blue color. Use this background as the standard value to check if the modified slides were also with a good background. To demonstrate the measuring result of the three-dimensional aerogel chips, 2-dimenetion chips will play the role of comparison. How the two-dimension chips modified with amino group (2% DAMO) should therefore be the first issue to be clarified. The modification procedure of the amino group on the slides is stated as followed: immerse glass slides in a staining container loaded with 2% of DAMO in ethanol solution for 4 hours. After washing the slides with double-distilled water, place the slides into an oven for 20 minutes. FIG. 14 showed that most of the background area was still in navy blue (deep blue) after the amino-group modification process. Although there appeared some small light-blue dots, the background was still acceptable.

Figure 15:
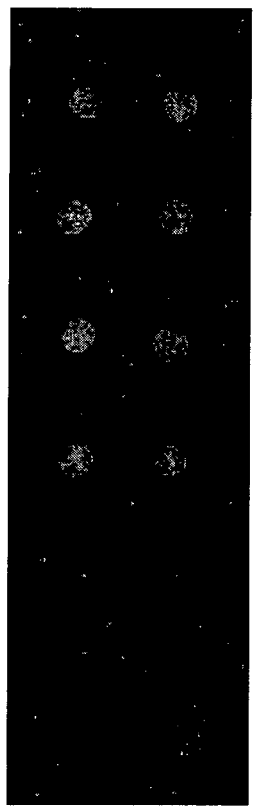
FIG. 15 shows the scanned image from the three-dimensional structure Biochip with dotting 10 wt % Aerogel dispersal solution.
Figure 16:
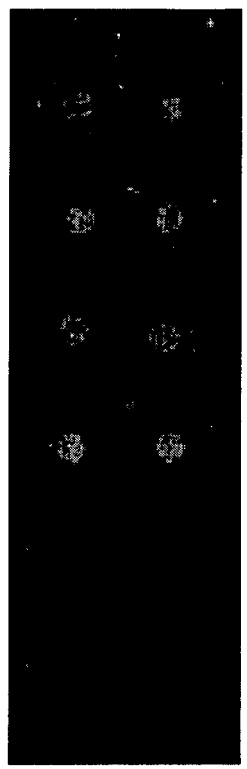
FIG. 16 shows the image of a three-dimension chip after the surface modification process according to a preferred example of the present invention.

FIG. 15 showed the scanned image from the three-dimensional biochip dropped with 10 wt % of aerogel dispersal solution. The round dots were the dropped aerogel. The image color was in light blue, which was still within a low background value. FIG. 16 showed turquoise (blue-green color) from the amino modified aerogel's surface.

Figure 17:
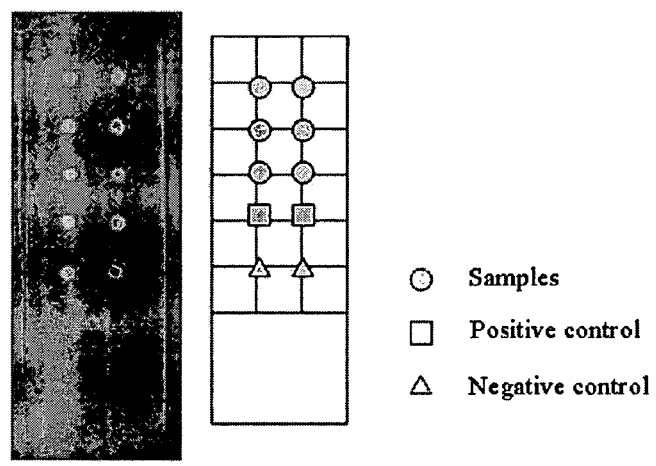
FIG. 17 shows the appearance picture of the slide with three-dimensional Aerogel structure according to a preferred example of the present invention.

FIG. 17 showed the appearance of the slide with the three-dimensional Aerogel structure. The sample dots in the evaluation region were prepared by the previous steps (1) to (7). Secondly, the positive control spot was the aerogel dot dropped only with amino-group modified quantum dots. The negative control spot was the unmodified aerogel. The purpose of the positive-control spot was to standardize different batches of biochips. It's possible that different batches of biochips could have uneven surface quality to result in deviated reading of signal intensities and make the data incomparable with one another. The positive-control spot was therefore used to standardize the detection result for different biochip batches and made the experimental results more meaningful. The role of the negative-control spot was to measure the background with the aerogel alone. The background can be deducted from result in further data analysis.

Figure 18:
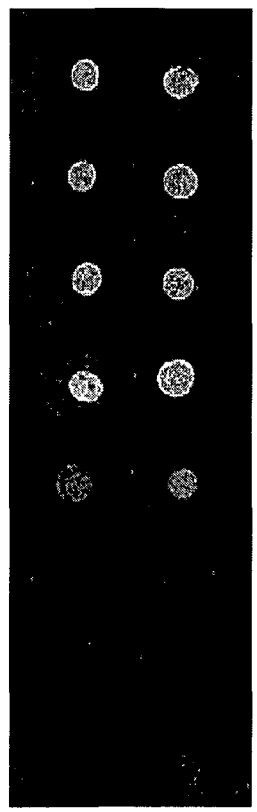
FIG. 18 shows the image of a three-dimension chip after immobilizing the capturing antibody according to a preferred example of the present invention.
Figure 19:
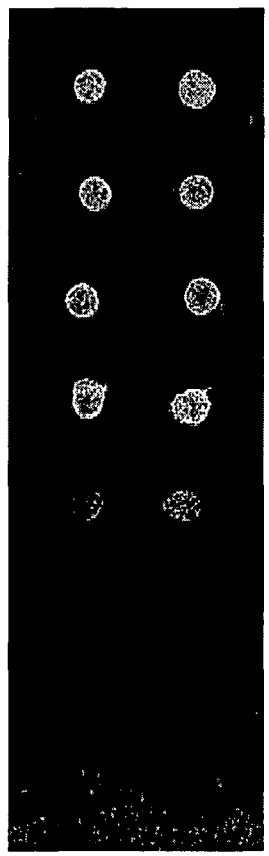
FIG. 19 shows the image of a three-dimension chip after the blocking reagent is applied according to a preferred example of the present invention.
Figure 20:
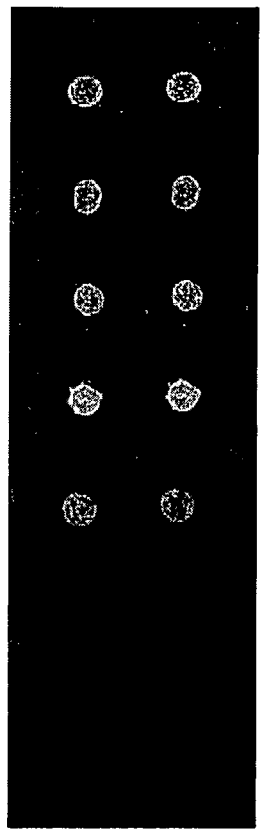
FIG. 20 shows the image of a three-dimension chip after the blocking step followed by applying the antigen (Human IL6) and washing off un-captured antigen.
Figure 21:
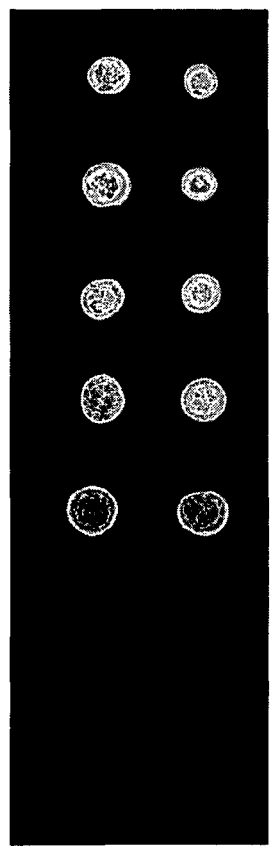
FIG. 21 shows the image of a three-dimension chip after applying the report antibody conjugated with the quantum dot, which is excited by a 533 nm laser light, and the un-binding report antibody is washed off.

FIG. 18 showed the background which was still in blue-green after dropping the capturing antibody (mouse anti-Human IL6). FIG. 19 showed the background was still in blue-green after the incubation and wash steps were applied. FIG. 20 showed that the background decreased slightly to light blue after dropping the antigen (Human IL6) on the top of the capturing antibody and washing off the uncaptured antigen. FIG. 21 showed that orange-yellow color was read from the report antibody (rabbit anti-human IL-6) labeled with the quantum dot at the end of the detection assay. This result indicated that the antibody-antigen sandwich immunoassay was carried out successfully.

Figure 22:
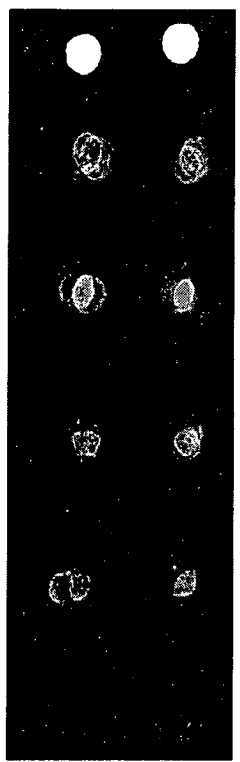
FIG. 22 shows the scanned image with the same immunoassay but on a two-dimensional biochip.

FIG. 22 showed the scanned image of a two-dimensional protein biochip with the identical immunoassay as the three-dimensional one for comparison.

The analysis software (GenePixPro6.0) was applied to analyze the signal on each sample spot on three-dimensional aerogel chips and 2-dimension protein chip. The result is listed in Tables 1 and 2.

Table 1 is the result of the three-dimensional aerogel chip shown as below:

| Sample spot | Antigen concentration, M | Intensity, OD | color |
|---|---|---|---|
| 1 | $1.44 \times 10^{-6}$ | 26213 | orange-yellow |
| 2 | $1.44 \times 10^{-6}$ | 28527 | orange-yellow |
| 3 | $1.44 \times 10^{-6}$ | 29041 | orange-yellow |
| 4 | $1.46 \times 10^{-6}$ | 31609 | orange-yellow |
| 5 | — | 11125 | blue |

Table 2 is the result of the 2-dimension protein chip shown as below:

| sample spot | Antigen concentration, M | Intensity, OD | color |
|---|---|---|---|
| 1 | 1.0 | 52029 | white |
| 2 | $1.0 \times 10^{-1}$ | 23130 | red |
| 3 | $1.0 \times 10^{-2}$ | 30067 | orange |
| 4 | $1.0 \times 10^{-3}$ | 22615 | green |
| 5 | $5.0 \times 10^{-4}$ | 16756 | blue |

According to Table 2, when the sample concentration reaches $5.0 \times 10^{-4}$M on the 2-dimension protein chip, the signal is around 16756, which is close to light-blue background value. We therefore predicted, by that reading, that a sample with concentration lower than $10^{-5}$ M will fall out the detectable region. When the concentration of three-dimensional Aerogel chip was with an antigen concentration as low as $1.44 \times 10^{-6}$M, the signal intensity was amplified to 26213~31609 by the Aerogel three-dimensional structure. It is thus evident that the huge surface area of the three-dimensional aerogel amplified the signal intensity.

Light modifications and variations are possibly developed from the above demonstrations. It is therefore needed to be understood that within the scope of the appended claims, the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming a biochip with a three-dimensional structure, comprising:
   providing a precursor solution comprising an ionic liquid, a hydrolysis catalyst, and at least one alkoxide monomer and/or aryloxide monomer, where the hydrolysis catalyst comprises one selected from the group consisting of the following or any combination of the following: acidic compound, and alkaline compound, and the precursor solution is formed by blendin the at least one alkoxide monomer and/or aryloxide monomer and the ionic liquid together to form a first mixture, adding the acidic compound to the first mixture to form a second mixture, and adding the alkaline compound to the second mixture to form the precursor solution;
   performing a blending process for the precursor solution to hydrolyze and polymerize the at least one alkoxide monomer and/or aryloxide monomer until the viscosity of the precursor solution reaches a specific viscosity more than or equal to 150 cps;
   setting the precursor solution to have the at least one alkoxide monomer and/or aryloxide monomer continue to undergo hydrolysis and condensation, so as to form a aerogel;
   performing an extracting process by a solvent for the aerogel to substitute the ionic liquid in pores of the aerogel;
   performing a freeze-drying process to remove the solvent in pores of the aerogel;
   performing a grinding process to grind the aerogel to form a aerogel powder;
   performing a modification process to introduce a specific moiety to the internal and external surfaces of the aerogel powder by mixing the aerogel powder with a modifier to form a modified aerogel powder;
   performing a coating process to coat and stabilize the modified aerogel powder on a specific region of a substrate, so as to form a biochip with a three-dimensional structure; and
   performing a converting process by providing a converter that comprises a first moiety and a second moiety and bonding the specific moiety of the aerogel powder with the first moiety of the converter to form a biochip having the second moiety on its surface;
   wherein the ionic liquid is formed by mixing an organic base with a Lewis acid that is not halogenated acid;
   the cationic moiety of organic base is selected from the group consisting of the following: 1-n-butyl-3-methylimidazolium (BMI), 1-octanyl-3-methylimidazolium (DMI), and 1-hexadecanyl-3-methylimidazolium (HDMI);
   the anionic moiety in the Lewis acid is selected from the group consisting of the following: $BF_4^-$, $PF_6^-$, $AsF_6^-$, $SbF_6^-$, $F(HF)_n^-$, $CF_3SO_3^-$, $CF_3CF_2CF_2SO_3^-$, $(CF_3SO_2)_2N^-$, $(CF_3SO_2)_3C^-$, $CF_3COO^-$, and $CF_3CF_2CF_2COO^-$; and
   the weight of the ionic liquid is about 50%~70% weight of the at least one alkoxide monomer and/or aryloxide monomer.

2. The method according to claim 1, wherein the coating process comprises:
   dispersing the modified aerogel powder in a double-distilled water to form a dispersing solution;
   coating the dispersing solution on a specific region of substrate; and
   performing a baking process to remove the solvent of the dispersing solution and to enhance the adhesive force between the modified aerogel powder and the substrate, so as to form the biochip with a three-dimensional structure.

3. The method according to claim 2, wherein the temperature of the baking process ranges from 80° C. to 120° C.

4. The method of claim 1, wherein the alkoxide monomer comprises a center element, which is Si.

5. The method according to claim 1, wherein the ionic liquid is a room temperature ionic liquid.

6. The method according to claim 1, wherein the material of the substrate comprises one selected from the group consisting of the following: silicon chip, glass, or polymer.

7. The method according to claim 1 wherein the alkoxide monomer of the aerogel comprises one selected from the group consisting of $SiO_2$, $TiO_2$, $V_2O_5$, $Al_2O_3$ and combinations thereof.

8. The method according to claim 1, wherein the diameter of the aerogel powder ranges about 10 nm to 250 nm.

9. The method according to claim 1, wherein the average pore diameter of the aerogel powder ranges about 2 nm to 50 nm.

10. The method according to claim 1, wherein the boiling point of the solvent is less than or equal to 200° C.

11. The method according to claim 1, wherein the solvent comprises one selected from the group consisting of the following: nitrile, alcohol, ketone, and water.

12. The method according to claim 1, wherein the modification process uses a modifier, and the modifier is an alkoxide monomer and/or aryloxide monomer with at least one specific moiety, and the specific moiety comprises one selected from the group consisting of the following: amine group, hydroxyl group, carboxyl group, and epoxy group.

13. The method according to claim 1, wherein the converter is proteins.

14. The method according to claim 1, wherein the method further comprises a blocking process after the converting process, and the blocking process comprises:
   providing a blocker that comprises a third moiety ; and
   bonding the specific moiety of the aerogel powder with the third moiety of the blacker to form a biochip having the second moiety on its surface.

15. The method according to claim 14, wherein the method further comprises a specific pairing process after the blocking process, and the specific pairing process comprises:
   providing a pair that comprises a fourth moiety and a fifth moiety; and
   bonding the second moiety of the biochip with the fourth moiety of the pair to form a biochip having the fifth moiety on its surface.

16. The method according to claim 15, wherein the pair is protein.

17. The method according to claim 15, wherein the method further comprises a labeling process after the specific pairing process, and the labeling process comprises:
   providing a labeling carrier that comprises a sixth moiety and a seventh moiety wherein conjugated with a marker; and
   bonding the fifth moiety of the pair labeling carrier with the sixth moiety of the labeling carrier to form a biochip having the marker on its surface.

18. The method according to claim 17, wherein the marker comprises one selected from the group consisting of the following: fluorescence substance, phosphorescence substance, luminescence substance, enzyme, radioactive element, quantum dot, nano diamond.

19. The method according to claim 17, wherein the labeling carrier comprises one selected from the group consisting of the following: antigens, primary antibody, labeling primary antibody, secondary antibodies, monoclonal antibodies, polyclonal antibodies, nucleic acids comprising monomeric and oligomeric types, proteins, enzymes, lipids, polysaccharides, sugars, peptides, polypeptides, drugs, viruses, microbes, and bioligands.

* * * * *